Figure 1:
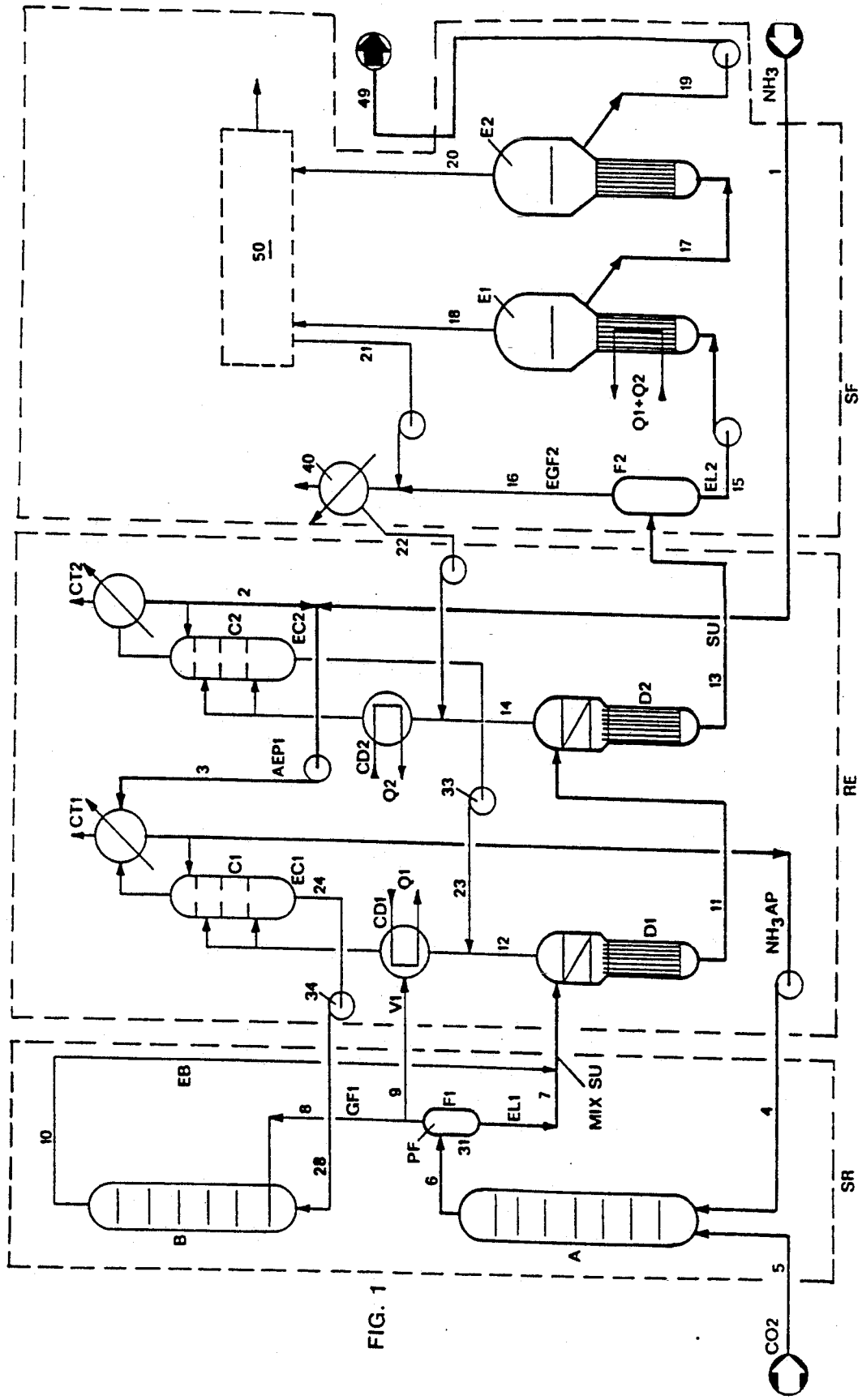

United States Patent
Pagani et al.

[11] Patent Number: 5,276,183
[45] Date of Patent: Jan. 4, 1994

[54] PROCESS AND PLANT FOR THE PRODUCTION OF UREA

[75] Inventors: Giorgio Pagani, Lugano; Umberto Zardi, Breganzona, both of Switzerland

[73] Assignee: Urea Casale S.A., Switzerland

[21] Appl. No.: 824,941

[22] Filed: Jan. 24, 1992

[30] Foreign Application Priority Data

Jan. 29, 1991 [CH] Switzerland ............ 00264/91

[51] Int. Cl.$^5$ ............................ C07C 273/04
[52] U.S. Cl. ........................ 564/67; 564/63; 564/69; 564/70; 564/71
[58] Field of Search ............ 564/67, 69, 71, 65, 564/70

[56] References Cited

U.S. PATENT DOCUMENTS

| | | | |
|---|---|---|---|
| 2,848,493 | 8/1957 | Dewling et al. | 564/67 |
| 4,354,040 | 10/1982 | Inoue et al. | 564/67 |
| 4,670,588 | 6/1987 | Zardi | 564/71 |

Primary Examiner—Richard L. Raymond
Assistant Examiner—Shailendra Kumar
Attorney, Agent, or Firm—Ostrolenk, Faber, Gerb & Soffen

[57] ABSTRACT

Process for the industrial synthesis of urea, in which ammonia ($NH_3$) and carbon dioxide ($CO_2$) are reacted in at least one reaction space SR at high temperature and pressure and the unreacted materials are treated in a recovery section, said synthesis comprising: a) a reaction between highly pure reagents; and b) a reaction between less pure reagents substantially recycled from said recovery section, characterized by the fact that reaction stage A for high Yield majority synthesis (HEPC), between very pure reagents, operating at a higher pressure (Pmax) for example above 300 kg/cm2 abs and preferably at about 400 kg/cm2 abs, is followed by a flash stage F1 operating at pressures lower by at least 40% than said pressure (Pmax) preferably lower than 200 kg/cm2 abs, the gas effluent GF1 from the above-mentioned flash stage F1 being fed to reaction stage B for minority synthesis of less pure reagents operating at a pressure below 200 kg/cm2 abs, while the liquid effluent EL1 from the abovementioned flash stage, together with effluent EB from stage B of minority reaction operating in parallel with majority reaction stage A, feeds a recovery section RE consisting of two decomposition stages D1 and D2 operating in series: the first D1 being at a pressure lower than 100 kg/cm2 abs preferably at 50 kg/cm2 abs; the second D2 operating at a pressure lower than 50 kg/cm2 abs preferably at 20 kg/cm2 abs.

12 Claims, 1 Drawing Sheet

PROCESS AND PLANT FOR THE PRODUCTION OF UREA

This invention concerns a process for the industrial synthesis of urea by reacting ammonia (NH3) and carbon dioxide (CO2) in at least one reaction space SR, at high temperature and pressure, recycling at least in part the unreacted products obtained in a recovery section.

More particularly the invention concerns a process as described above in which: a) very pure reagents undergo a synthesis reaction; and b) a synthesis reaction takes place between less pure reagents, substantially recycled from said recovery section (recovery mixture).

A system for the synthesis of urea of the type described above has been described in Swiss Patent Application No. 03216/90-1 lodged on Oct. 3, 1990 by the Applicants.

The plant for carrying out this process comprises: a first high yield reactor fed from the outside with fresh CO2 and NH3 and with very pure recovery NH3; a second reactor, parallel with the first, and with a less high yield than the first, fed substantially with reagents from the recovery mixture; and a system or section for the recovery of reaction mixtures obtained from said first and second reactor.

Continuing their research and experiments in this important technical sector, the Applicants have now perfected, not without surprise, an embodiment of the process according to the said main patent application, which lends itself to being put into effect in a particularly efficient and advantageous manner, above all because of the small investment and minimum consumption of energy it requires.

In effect it has been found that the solution of urea coming from the two reaction spaces or stages in parallel for the recycling of the unreacted products (residual carbamate and NH3 excess) can be treated economically without making use of the well-known costly and complex stripping processes with NH3 and CO2.

In the process according to this invention, and more particularly in its application when building new plants, reaction stage A for majority high Yield synthesis (HEPC) between very pure reagents, operating at a higher pressure (Pmax) for example greater than 300 kg/cm2 abs and by preference about 400 kg/cm2 abs, is followed by a flash stage F1 operating at pressures lower by at least 40% than the said pressure (Pmax) and by preference at about 200 kg/cm2 abs, the gas effluent GF1 from said flash stage F1 being fed to reaction stage B of minority synthesis of the less pure reagents operating at a pressure smaller than 200 kg/cm2 abs, while the liquid effluent EL1 from the above-mentioned flash stage, together with effluent EB from the minority reaction stage B operating in parallel with the majority reaction stage A, feeds a recovery section RE consisting in two decomposition stages D1 and D2 in series: the first D1 being at a pressure lower than 100 kg/cm2 abs and by preference at 50 kg/cm2 abs; the second D2 operating at a pressure lower than 50 kg/cm2 abs and by preference at 20 kg/cm2 abs.

In an extremely simple and efficient embodiment each decomposition stage consists of decomposer D1 and D2 respectively (heat exchanger for the distillation of reagents not transformed into urea), whose gas effluents consisting of NH3+CO2+H2O feed a condensation system with direct heat recovery from the process, where the partial condensation of said effluents is carried out and then completed in a fractionating column with a head condenser.

The various aspects and advantages of the invention will be better illustrated by the following description of one of the possible embodiments, preferred but not limitative, shown in the attached drawing (FIG. 1) which is an illustration of the process and of the related plant.

In this scheme A shows the main synthesis reaction space or stage, where are made to flow the very pure fresh reagents coming substantially from outside, as CO2 from line 5 and NH3 from line 4. The reaction in A takes place at the highest pressure of the whole system (Pmax), by preference above 300 kg/cm2 abs, and even better at about 400 kg/cm2 abs. The products of the main reaction in A leaving on line 6 undergo flash F1 in apparatus 31 operating at a pressure PF which is lower by at least 40% than (Pmax) and which by preference is lower than 200 kg/cm2 abs. The gas effluent GF1 from flash stage F1 feeds through line 8 the second space B for the synthesis reaction of the less pure reagents (recovery) which is also operating at a pressure lower than (Pmax), practically the same as PF, i.e. lower than 200 kg/cm2 abs.

According to an aspect of the invention the liquid effluent from EL1 from flash stage F1 feeds through line 7, together with effluent EB from stage B on line 10, a recovery section RE comprising two decomposition stages D1 and D2 operating in series with line 11 which therefore connects the bottom of D1 with the top of D2. The first decomposer D1 (or heat exchanger) is at a pressure lower than 100 kg/cm2 abs but not below 40 and preferably at about 50 kg/cm2 abs while the second stage D2 (of decomposition or heat exchange) is at a pressure lower than 50 kg/cm2 abs, preferably at about 20 kg/cm2 abs.

The two above stages D1 and D2 carry out the distillation of reagents unreacted in A and B and their gas effluents 12 respectively 14 consisting substantially of NH3+CO2+H2O feed a condensation system with heat exchange directly from the process (precondenser CD1, respectively CD2, "process to process") where partial condensation of said effluents takes place, condensation which is completed in fractionating column C1, respectively C2, with head condenser (CT1 respectively CT2) to recover highly pure ammonia NH3 AP. This substantially pure ammonia is recycled to main reaction stage A (line 4).

The bottom effluent EC1 from column C1 of the first stage of decomposition D1, consisting of a more concentrated carbamate solution, is fed through line 24, pump 34 and line 28 to the second reaction space B, while the product of condensation EC2 at the bottom of column C2, consisting of a less concentrated carbamate solution, is recycled through pump 33, line 23 and precondenser CD1 to column C1 of the first stage, together with vapours V1 from the first decomposer D1.

The urea solution SU from the second treatment stage D2 is carried along line 13 and undergoes a flash treatment F2 by preference adiabatic at a pressure lower than 20 kg/cm2 abs, by preference lower than 10 kg/cm2 abs, and better still between 3 and 6 kg/cm2 abs; the gas effluent EGF2 on line 16, after being condensed in condenser 40 is fed, through line 22, pump 32 and precondenser CD2 to column C2 of the second stage of treatment, while liquid effluent EL2 (solution of purified urea) is sent to the final vacuum concentration, classically carried out for example in evaporators E1 and E2. The heat Q1 and Q2 recovered in CD1 and CD2 is exchanged preferably in E1 ("process to process") for the concentration of urea which finally leaves from line 19 and pumped in 39 it collects in 49. The vacuum and condensate treatment system 50 (conventional) receives vapours from the heads of E1 and E2 and supplies recovery ammonia water on line 21.

It has been found that the process according to the invention is particularly efficient and has really novel important aspects when about 80% of the urea is produced in the high yield reactor A (HEPC), while the remaining 20% is produced in the secondary reaction space B or service reactor RS. This becomes evident from the following examples, which are absolutely non limitative as regards the process.

Examples 1 and 2

In a specific case the project data were:

| | |
|---|---|
| capacity | 1500 MTD urea |
| compression of $CO_2$ at 150 kg/cm2 abs in a steam turbine centrifugal machine power steam for the turbine with extraction at 13 kg/cm2 abs for the process: | |
| pressure | 43 kg/cm2 abs |
| temperature | 390° C. |
| condensation pressure | 0.12 kg/cm2 abs |

The heat rates for the turbine are:

| | |
|---|---|
| 43 kg/cm2 abs–13.00 kg/cm2 abs | 16.4 kg/kWh |
| 43 kg/cm2 abs–0.12 kg/cm2 abs | 4.1 kg/kWh |
| 43 kg/cm2 abs–4.50 kg/cm2 abs | 8.7 kg/kWh |

According to the invention 80% of urea was produced in high Yield HEPC reactor A, while the remaining 20% was obtained in the B service reactor RS.

For reactor B two possible cases have been considered:
- Case A with a molar ratio $H_2O/CO_2 = 1$ and a yield of 64%
- Case B with a molar ratio $H_2O/CO_2 = 1.2$ and a yield of 62%

In adopting the simplified process scheme according to FIG. 1 the material balances calculated are shown in Table 1 and 2, pages 1 and 2 respectively.

It should be noted that, for simplicity's sake, inert materials possibly present in the $CO_2$ and passivating air (the amount of air to be introduced into the $CO_2$ is equal to 1000÷2000 ppm vol. of $O_2$ in the $CO_2$ itself), are not indicated.

Moreover, it is assumed that the formation of by-products and the losses towards the outside are nil.

The process technical characteristics are:

| Reactor A (HEPC) | | |
|---|---|---|
| capacity | 1200 MTD urea | |
| $NH_3/CO_2$ mol | 4.5 | |
| $H_2O/CO_2$ mol | 0 | |
| yield | 80% | |
| temperature | 215° C. | |
| pressure | 400 kg/cm2 abs | |
| Reactor B (RS) | Case I | Case II |
| capacity | 300 MTD urea | 300 MTD urea |
| $NH_3/CO_2$ mol | 4.0 | 4.0 |
| $H_2O/CO_2$ mol | 1.0 | 1.2 |
| yield | 64% | 62% |
| temperature | 190° C. | 190° C. |
| pressure | 140 kg/cm2 abs | 140 kg/cm2 abs |

The average weight yield is 76.8% in Case I and 76.4 in Case II.

A short description of the process follows below, still with reference to FIG. 1.

The process is in three distinct sections, viz.:
- a reaction section SR consisting of the two synthesis reactors HEPC (A) and RS (B), in which part of the flash vapours obtained by flashing the solution from A (HEPC) at 140 kg/cm2 is fed to reactor B (RS) and, together with the recycled carbamate solution, forms its feed;
- a medium pressure section RE in which are treated a part of the above-mentioned flash vapours and the mix SU of the urea solutions from the two reactors A and B.

The composition of the mix solution is:

| | Case I | Case II |
|---|---|---|
| UR | 47.27% weight | 46.36% weight |
| $NH_3$ | 27.41% weight | 27.42% weight |
| $CO_2$ | 7.89% weight | 8.08% weight |
| $H_2O$ | 17.43% weight | 18.14% weight |
| | 100.00% weight | 100.00% weight |

Apart from the remarkably smaller amount of $H_2O$, this solution is similar to that which can be obtained in a Snamprogetti-type stripper and corresponds to a hypothetical reactor with the following characteristics:

| | Case I | Case II |
|---|---|---|
| $NH_3/CO_2$ mol | 3.3 | 3.3 |
| $H_2O/CO_2$ mol | 0.19 | 0.24 |
| reactor efficiency | 81.5% | 80.8% |

It can be easily understood how the treatment of this solution can be relatively simple and inexpensive in terms of energy consumption.

The solution is to be distilled in two stages (D1 and D2) at 50 kg/cm2 abs and 18 kg/cm2 abs respectively, each stage having a precondenser (CD1 and CD2) and a fractionating column (C1 and C2) for very pure $NH_3$.

More particularly, in stage D1 at 50 kg/cm2 abs the precondenser (which, as already mentioned, receives part of the flash vapours) is connected, according to double-effect technique, to the 1st vacuum distiller E1 and to the section where process water is treated, while, the head condenser permits the preheating at about 80° C. of all the $NH_3$ sent to HEPC.

In stage D2 at 18 kg/cm2 abs the heat available in the precondenser is used, still in accordance with the double-effect technique, in the lower part of the 1st vacuum distiller.

- a finishing section SF in which, after the adiabatic flash F2 of the solution at 5 kg/cm2 abs, the urea solution SU is vacuum distilled according to conventional techniques.

It should be noted that in the 1st vacuum distiller the urea solution is concentrated up to 96% by using the "process to process" vapours condensation heat.

Reactor A (HEPC), which is relatively small, (0.05 m3/TD urea), is lined internally with zirconium so as to eliminate any possibility of corrosion due to the high operating temperature.

Several reactors of this type have been used for decades and some of them are still in operation without any problems.

Alternatively, it is possible to dispense with the zirconium lining by using an internal lining in 2RE69 cooled with the feed NH3 according to the Applicants' Patent Application 03216/90-1.

This shows the following consumption:

|  | Case I | Case II |
|---|---|---|
| steam at 43 kg/cm2 abs and 390° C. | 759 kg/MT urea | 772 kg/MT urea |
| electric power | 65 kWh/MT urea | 65 kWh/MT urea |

The increase in the molar ratio H2O/CO2 in reactor B (RS) hardly increases steam consumption, while increasing its reliability.

Steam consumption indicated includes also steam required for the turbine operating centrifugal compressor for CO2 (the CO2 is compressed from 1 to 150 kg/cm2 abs in a centrifugal machine and from 150 to 400 kg/cm2 abs in an alternating compressor), while energy consumption includes the energy used for the compression of CO2 from 150 to 400 kg/cm2 abs.

On the basis of the above, it can be said that the new process seems to be very interesting for the following reasons:
- technology fully tried on an industrial scale;
- low energy consumption;
- remarkable simplicity;
- no "difficult" apparatus such as strippers and carbamate condensers required;
- low investment cost.

It is because of its very simplicity that the new process can be profitably adopted not only in large plants but also in medium- and small-size plants.

TABLE 1

NEW PLANT - 1500 MTD UREA - CASO I

| LINE | 1 | | 2 | | 3 | | 4 | | 5 | | 6 | |
|---|---|---|---|---|---|---|---|---|---|---|---|---|
| Physical State | liquid | | liquid | | liquid | | liquid | | gas | | liquid | |
| P (kg/cm² abs) | 20 | | 20 | | 50 | | 400 | | 400 | | 400 | |
| T (°C.) | 40 | | 40 | | 40 | | 75 | | 150 | | 215 | |
| COMPOSITION | kg/h | % w | kg/h | % w | kg/h | % w | kg/h | % w | kg/h | % w | kg/h | % w |
| Urea | | 0 | | 0 | | 0 | | 0 | | 0 | 50000 | 39.83 |
| Biuret | | 0 | | 0 | | 0 | | 0 | | 0 | | 0 |
| NH3 | 35417 | 100 | 15954 | 100 | 51371 | 100 | 79689 | 100 | | 0 | 51355 | 40.91 |
| CO2 | | 0 | | 0 | | 0 | | 0 | 45833 | 100 | 9167 | 7.30 |
| H2O | | 0 | | 0 | | 0 | | 0 | | 0 | 15000 | 11.95 |
| TOTAL | 35417 | 100 | 15954 | 100 | 51371 | 100 | 79689 | 100 | 45833 | 100 | 125522 | 100 |
| Inerts | | | | | | | | | | | | |
| O2 | | | | | | | | | | | | |

| LINE | 7 | | 8 | | 9 | | 10 | | 11 | | 12 | |
|---|---|---|---|---|---|---|---|---|---|---|---|---|
| Physical State | liquid | | vapour | | vapour | | liquid | | liquid | | vapour | |
| P (kg/cm² abs) | 140 | | 140 | | 140 | | 140 | | 50 | | 50 | |
| T (°C.) | 200 | | 200 | | 200 | | 190 | | 170 | | 150 | |
| COMPOSITION | kg/h | % w | kg/h | % w | kg/h | % w | kg/h | % w | kg/h | % w | kg/h | % w |
| Urea | 50000 | 55.61 | | 0 | | 0 | 12500 | 29.54 | 62500 | 58.40 | | 0 |
| Biuret | | 0 | | 0 | | 0 | | 0 | | 0 | | 0 |
| NH3 | 21192 | 23.57 | 11011 | 84.70 | 19152 | 84.71 | 15052 | 35.57 | 19139 | 17.88 | 17105 | 67.88 |
| CO2 | 5278 | 5.87 | 1420 | 10.92 | 2469 | 10.92 | 5154 | 12.18 | 3190 | 2.98 | 7242 | 28.74 |
| H2O | 13442 | 14.95 | 569 | 4.38 | 989 | 4.37 | 9610 | 22.71 | 22200 | 20.74 | 852 | 3.38 |
| TOTAL | 89912 | 100 | 13000 | 100 | 22610 | 100 | 42316 | 100 | 107029 | 100 | 25199 | 100 |
| Inerts | | | | | | | | | | | | |
| O2 | | | | | | | | | | | | |

| LINE | 13 | | 14 | | 15 | | 16 | | 17 | | 18 | |
|---|---|---|---|---|---|---|---|---|---|---|---|---|
| Physical State | liquid | | vapour | | liquid | | vapour | | liquid | | vapour | |
| P (kg/cm² abs) | 18 | | 18 | | 5 | | 5 | | 0.35 | | 0.35 | |
| T (°C.) | 160 | | 150 | | 140 | | 130 | | 130 | | 130 | |
| COMPOSITION | kg/h | % w | kg/h | % w | kg/h | % w | kg/h | % w | kg/h | % w | kg/h | % w |
| Urea | 62500 | 71.68 | | 0 | 62500 | 73.80 | | 0 | 62500 | 96.00 | | 0 |
| Biuret | | 0 | | 0 | | 0 | | 0 | | 0 | | 0 |
| NH3 | 2604 | 2.99 | 16535 | 83.38 | 1263 | 1.49 | 1341 | 53.34 | 13 | .02 | 1250 | 6.38 |
| CO2 | 694 | .80 | 2496 | 12.59 | 421 | .50 | 273 | 10.86 | 7 | .01 | 414 | 2.11 |
| H2O | 21400 | 24.54 | 800 | 4.03 | 20500 | 24.21 | 900 | 35.80 | 2585 | 3.97 | 17915 | 91.50 |
| TOTAL | 87198 | 100 | 19831 | 100 | 84684 | 100 | 2514 | 100 | 65105 | 100 | 19579 | 100 |
| Inerts | | | | | | | | | | | | |
| O2 | | | | | | | | | | | | |

| LINE | 19 | | 20 | | 21 | | 22 | | 23 | | 24 | |
|---|---|---|---|---|---|---|---|---|---|---|---|---|
| Physical State | liquid | | vapour | | liquid | | liquid | | liquid | | liquid | |
| P (kg/cm² abs) | 0.05 | | 0.05 | | 3 | | 3 | | 17 | | 50 | |
| T (°C.) | 140 | | 140 | | 40 | | 40 | | 120 | | 145 | |
| COMPOSITION | kg/h | % w | kg/h | % w | kg/h | % w | kg/h | % w | kg/h | % w | kg/h | % w |
| Urea | 62500 | 99.70 | | 0 | | 0 | | 0 | | 0 | | 0 |
| Biuret | | 0 | | 0 | | 0 | | 0 | | 0 | | 0 |
| NH3 | | | 13 | .54 | 1263 | 36.78 | 2604 | 43.78 | 3185 | 32.42 | 11124 | 37.95 |
| CO2 | | | 7 | .29 | 421 | 12.26 | 694 | 11.67 | 3190 | 32.47 | 12901 | 44.01 |
| H2O | 188 | .30 | 2397 | 99.17 | 1750 | 50.96 | 2650 | 44.55 | 3450 | 35.11 | 5291 | 18.05 |
| TOTAL | 62688 | 100 | 2417 | 100 | 3434 | 100 | 5948 | 100 | 9825 | 100 | 29316 | 100 |

TABLE 1-continued

NEW PLANT - 1500 MTD UREA - CASO I

| LINE | 25 | | 26 | | 27 | | 28 | | 29 | | 30 | |
|---|---|---|---|---|---|---|---|---|---|---|---|---|
| Physical State | | | | | | | | | | | | |
| P (kg/cm² abs) | | | | | | | | | | | | |
| T (°C) | | | | | | | | | | | | |
| COMPOSITION | kg/h | % w | kg/h | % w | kg/h | % w | kg/h | % w | kg/h | % w | kg/h | % w |
| Urea | | 0 | | 0 | | 0 | | 0 | | 0 | | 0 |
| Biuret | | 0 | | 0 | | 0 | | 0 | | 0 | | 0 |
| $NH_3$ | | 0 | | 0 | | 0 | | 0 | | 0 | | 0 |
| $CO_2$ | | 0 | | 0 | | 0 | | 0 | | 0 | | 0 |
| $H_2O$ | | 0 | | 0 | | 0 | | 0 | | 0 | | 0 |
| TOTAL | 0 | 0 | 0 | 0 | 0 | 0 | 0 | 0 | 0 | 0 | 0 | 0 |
| Inerts | | | | | | | | | | | | |
| $O_2$ | | | | | | | | | | | | |

| LINE | 31 | | 32 | |
|---|---|---|---|---|
| Physical State | | | | |
| P (kg/cm² abs) | | | | |
| T (°C) | | | | |
| COMPOSITION | kg/h | % w | kg/h | % w |
| Urea | | 0 | | 0 |
| Biuret | | 0 | | 0 |
| $NH_3$ | | 0 | | 0 |
| $CO_2$ | | 0 | | 0 |
| $H_2O$ | | 0 | | 0 |
| TOTAL | 0 | 0 | 0 | 0 |
| Inerts | | | | |
| $O_2$ | | | | |

TABLE 2

NEW PLANT - 1500 MTD UREA - CASO II

| LINE | 1 | | 2 | | 3 | | 4 | | 5 | | 6 | |
|---|---|---|---|---|---|---|---|---|---|---|---|---|
| Physical State | liquid | | liquid | | liquid | | liquid | | gas | | liquid | |
| P (kg/cm² abs) | 20 | | 20 | | 50 | | 400 | | 400 | | 400 | |
| T (°C) | 40 | | 40 | | 40 | | 75 | | 150 | | 215 | |
| COMPOSITION | kg/h | % w | kg/h | % w | kg/h | % w | kg/h | % w | kg/h | % w | kg/h | % w |
| Urea | | 0 | | 0 | | 0 | | 0 | | 0 | 50000 | 39.83 |
| Biuret | | 0 | | 0 | | 0 | | 0 | | 0 | | 0 |
| $NH_3$ | 35417 | 100 | 15954 | 100 | 51371 | 100 | 79689 | 100 | | 0 | 51355 | 40.91 |
| $CO_2$ | | 0 | | 0 | | 0 | | 0 | 45833 | 100 | 9167 | 7.30 |
| $H_2O$ | | 0 | | 0 | | 0 | | 0 | | 0 | 15000 | 11.95 |
| TOTAL | 35417 | 100 | 15954 | 100 | 51371 | 100 | 79689 | 100 | 45833 | 100 | 125522 | 100 |
| Inerts | | | | | | | | | | | | |
| $O_2$ | | | | | | | | | | | | |

| LINE | 7 | | 8 | | 9 | | 10 | | 11 | | 12 | |
|---|---|---|---|---|---|---|---|---|---|---|---|---|
| Physical State | liquid | | vapour | | vapour | | liquid | | liquid | | vapour | |
| P (kg/cm² abs) | 140 | | 140 | | 140 | | 140 | | 50 | | 50 | |
| T (°C) | 200 | | 200 | | 200 | | 190 | | 170 | | 150 | |
| COMPOSITION | kg/h | % w | kg/h | % w | kg/h | % w | kg/h | % w | kg/h | % w | kg/h | % w |
| Urea | 50000 | 55.61 | | 0 | | 0 | 12500 | 27.84 | 62500 | 57.76 | | 0 |
| Biuret | | 0 | | 0 | | 0 | | 0 | | 0 | | 0 |
| $NH_3$ | 21192 | 23.57 | 11011 | 84.70 | 19152 | 84.71 | 15767 | 35.12 | 19139 | 17.69 | 17820 | 67.00 |
| $CO_2$ | 5278 | 5.87 | 1420 | 10.92 | 2469 | 10.92 | 5618 | 12.51 | 3654 | 3.38 | 7242 | 27.23 |
| $H_2O$ | 13442 | 14.95 | 569 | 4.38 | 989 | 4.37 | 11008 | 24.52 | 22915 | 21.18 | 1535 | 5.77 |
| TOTAL | 89912 | 100 | 13000 | 100 | 22610 | 100 | 44893 | 100 | 108208 | 100 | 26597 | 100 |
| Inerts | | | | | | | | | | | | |
| $O_2$ | | | | | | | | | | | | |

| LINE | 13 | | 14 | | 15 | | 16 | | 17 | | 18 | |
|---|---|---|---|---|---|---|---|---|---|---|---|---|
| Physical State | liquid | | vapour | | liquid | | vapour | | liquid | | vapour | |
| P (kg/cm² abs) | 18 | | 18 | | 5 | | 5 | | 0.35 | | 0.35 | |
| T (°C) | 160 | | 150 | | 140 | | 130 | | 130 | | 130 | |
| COMPOSITION | kg/h | % w | kg/h | % w | kg/h | % w | kg/h | % w | kg/h | % w | kg/h | % w |
| Urea | 62500 | 71.68 | | 0 | 62500 | 73.80 | | 0 | 62500 | 96.00 | | 0 |
| Biuret | | 0 | | 0 | | 0 | | 0 | | 0 | | 0 |
| $NH_3$ | 2604 | 2.99 | 16535 | 78.70 | 1263 | 1.49 | 1341 | 53.34 | 13 | .02 | 1250 | 6.38 |
| $CO_2$ | 694 | .80 | 2960 | 14.09 | 421 | .50 | 273 | 10.86 | 7 | .01 | 414 | 2.11 |
| $H_2O$ | 21400 | 24.54 | 1515 | 7.21 | 20500 | 24.21 | 900 | 35.80 | 2585 | 3.97 | 17915 | 91.50 |
| TOTAL | 87198 | 100 | 21010 | 100 | 84684 | 100 | 2514 | 100 | 65105 | 100 | 19579 | 100 |
| Inerts | | | | | | | | | | | | |
| $O_2$ | | | | | | | | | | | | |

| LINE | 19 | 20 | 21 | 22 | 23 | 24 |
|---|---|---|---|---|---|---|

TABLE 2-continued

NEW PLANT - 1500 MTD UREA - CASO II

| Physical State | liquid | | vapour | | liquid | | liquid | | liquid | | liquid | |
|---|---|---|---|---|---|---|---|---|---|---|---|---|
| P (kg/cm² abs) | 0.05 | | 0.05 | | 3 | | 3 | | 17 | | 50 | |
| T (°C.) | 140 | | 140 | | 40 | | 40 | | 120 | | 145 | |
| COMPOSITION | kg/h | % w | kg/h | % w | kg/h | % w | kg/h | % w | kg/h | % w | kg/h | % w |
| Urea | 62500 | 99.70 | | 0 | | 0 | | 0 | | 0 | | 0 |
| Biuret | | 0 | | 0 | | 0 | | 0 | | 0 | | 0 |
| NH3 | | 0 | 13 | .54 | 1263 | 36.78 | 2604 | 43.78 | 3185 | 28.94 | 11839 | 37.12 |
| CO2 | | 0 | 7 | .29 | 421 | 12.26 | 694 | 11.67 | 3654 | 33.21 | 13365 | 41.91 |
| H2O | 188 | .30 | 2397 | 99.17 | 1750 | 50.96 | 2650 | 44.55 | 4165 | 37.85 | 6689 | 20.97 |
| TOTAL | 62688 | 100 | 2417 | 100 | 3434 | 100 | 5948 | 100 | 11004 | 100 | 31893 | 100 |
| Inerts | | | | | | | | | | | | |
| O2 | | | | | | | | | | | | |

| LINE | 25 | | 26 | | 27 | | 28 | | 29 | | 30 | |
|---|---|---|---|---|---|---|---|---|---|---|---|---|
| Physical State | | | | | | | | | | | | |
| P (kg/cm² abs) | | | | | | | | | | | | |
| T (°C.) | | | | | | | | | | | | |
| COMPOSITION | kg/h | % w | kg/h | % w | kg/h | % w | kg/h | % w | kg/h | % w | kg/h | % w |
| Urea | | 0 | | 0 | | 0 | | 0 | | 0 | | 0 |
| Biuret | | 0 | | 0 | | 0 | | 0 | | 0 | | 0 |
| NH3 | | 0 | | 0 | | 0 | | 0 | | 0 | | 0 |
| CO2 | | 0 | | 0 | | 0 | | 0 | | 0 | | 0 |
| H2O | | 0 | | 0 | | 0 | | 0 | | 0 | | 0 |
| TOTAL | 0 | 0 | 0 | 0 | 0 | 0 | 0 | 0 | 0 | 0 | 0 | 0 |
| Inerts | | | | | | | | | | | | |
| O2 | | | | | | | | | | | | |

| LINE | 31 | | 32 | |
|---|---|---|---|---|
| Physical State | | | | |
| P (kg/cm² abs) | | | | |
| T (°C.) | | | | |
| COMPOSITION | kg/h | % w | kg/h | % w |
| Urea | | 0 | | 0 |
| Biuret | | 0 | | 0 |
| NH3 | | 0 | | 0 |
| CO2 | | 0 | | 0 |
| H2O | | 0 | | 0 |
| TOTAL | 0 | 0 | 0 | 0 |
| Inerts | | | | |
| O2 | | | | |

We claim:

1. A process for the synthesis of urea in a plant including at least one reaction space for reacting ammonia and carbon dioxide at high temperature and pressure and a recovery section for recovering unreacted reagents, comprising the steps of:
   (a) reacting highly pure ammonia and carbon dioxide in a first reactor at a predetermined pressure above 300 kg/cm² abs and temperature sufficient to carry out the reaction and reacting less pure ammonia and carbon dioxide recycled from the recovery section in a second reactor at a pressure less than 200 kg/cm² abs and temperature sufficient to carry out the reaction, the predetermined pressure being greater than the pressure in the second reactor;
   (b) flash separating a product stream from the first reactor at a pressure at least 40% lower than the pressure in the first reactor into a gaseous effluent and a liquid effluent;
   (c) feeding the gaseous effluent to the second reactor and feeding the liquid effluent together with the effluent from said second reactor to the recovery section, decomposing the liquid effluent in the recovery section and withdrawing a urea solution therefrom.

2. The process of claim 1, wherein the first reactor operates at a pressure of about 400 kg/cm² abs.

3. The process of claim 1, wherein the flash separation operates at a pressure less than 200 kg/cm² abs.

4. The process of claim 1, wherein the second decomposition stage operates at a pressure lower than 50 kg/cm² abs.

5. The process of claim 4, wherein the second decomposition stage operates at a pressure of 20 kg/cm² abs.

6. The process of claim 1, wherein 80% of the urea is produced in the first reactor and 20% of the urea is produced in the second reactor.

7. The process of claim 6, further comprising the step of condensing a gaseous effluent including ammonia, carbon dioxide and water from each decomposition stage to recover a highly pure ammonia stream and recycling the highly pure ammonia stream from the first decomposition stage to the first reactor.

8. The process of claim 1, further comprising the step of condensing a gaseous effluent including ammonia, carbon dioxide and water from each decomposition stage to recover a highly pure ammonia stream and recycling the highly pure ammonia stream from the first decomposition stage to the first reactor.

9. The process of claim 8, further comprising the steps of recovering a carbamate stream from the first decomposition stage and feeding the carbamate stream to the second reactor, and recovering a second carbamate stream from the second decomposition stream and combining the second carbamate stream with the gaseous effluent from the first decomposition stage.

10. The process of claim 9, further comprising the step of heating a portion of the highly pure ammonia stream from the second decomposition stage using heat from the first decomposition stage and recycling the heated portion of the highly pure ammonia stream to the first reactor.

11. The process of claim 10, further comprising the step of recovering a urea solution from the second decomposition stage and flash separating the recovered urea solution at a pressure less than 10 kg/cm$^2$ abs into a gaseous effluent and a solution of purified urea, condensing the gaseous effluent to form a weak carbamate solution and recycling the weak carbamate solution to the second decomposition stage, and concentrating the solution of purified urea to form a urea product.

12. The process of claim 1, wherein said recovery section consists of two decomposition stages operating in series to distill ammonia and carbon dioxide not transformed into urea, a first decomposition stage operating at a pressure lower than 100 kg/cm$^2$ abs and a second decomposition stage operating at a pressure lower than 50 kg/cm$^2$, and the urea containing product is withdrawn from the second decomposition stage.

* * * * *